US005755230A

United States Patent [19]
Schmidt et al.

[11] Patent Number: 5,755,230
[45] Date of Patent: May 26, 1998

[54] WIRELESS EEG SYSTEM FOR EFFECTIVE AUDITORY EVOKED RESPONSE

[75] Inventors: Robert N. Schmidt, Cleveland; James R. Buckett, Chagrin Falls; Steven P. Hendrix, Sagamore Hills, all of Ohio

[73] Assignee: Cleveland Medical Devices Inc., Cleveland, Ohio

[21] Appl. No.: 529,646

[22] Filed: Sep. 18, 1995

[51] Int. Cl.$^6$ ................................. A61B 5/0476
[52] U.S. Cl. ........................................... 128/731
[58] Field of Search ........................ 128/731, 732, 128/746, 640, 644, 639, 903, 904

[56] References Cited

U.S. PATENT DOCUMENTS

| | | | |
|---|---|---|---|
| 4,681,111 | 7/1987 | Silvian | 128/697 X |
| 5,230,344 | 7/1993 | Ozdamar et al. | 128/731 |
| 5,307,817 | 5/1994 | Guggenbuhl et al. | 128/696 |

OTHER PUBLICATIONS

Sid Deutsch, Multielectrode EEG Biotelemetry: Remote Monitoring and Stimulation of Ambulatory Monkeys and Humans, Conference Paper, pp. 162–167, Oct. 1977.

*Primary Examiner*—Jennifer Bahr
*Assistant Examiner*—Samuel Gilbert
*Attorney, Agent, or Firm*—Robert N. Schmidt; John H. Vynalek

[57] ABSTRACT

A wireless EEG system for effective auditory evoked response, comprising an electrode array which is adapted to be attached to a person and senses voltages produced by the brain electrical activity of the person; transmitter electrically connected to the electrode array such that the transmitter produces a radio frequency signal corresponding to the voltages sensed by the electrode array, encodes the radio frequency signal with error correcting encoding and transmits the radio frequency signal by radio frequency telemetry through a transmitting antenna; the transmitter utilizing carrier frequency shift keyed circuitry to modulate a phase locked loop synthesized carrier frequency and reference frequency shift keyed circuitry to modulate a reference frequency to allow for non-return to zero format of the radio frequency signal obviating the need for Manchester encoding; receiver that receives through a receiving antenna the radio frequency signal produced and transmitted by the transmitter and whereby the receiver decodes the radio frequency signal and produces a data output corresponding to the radio frequency signal received by the receiver; and an operator interface connected to the receiver such that the operator interface receives as input the data output produced by the receiver such that the operator interface records a verbal stimulus given by an individual and provides an auditory stimulus whereby the operator interface displays the data output, such display providing a comparison of the brain electrical activity in response to said stimulus.

22 Claims, 3 Drawing Sheets

WIRELESS EEG SYSTEM FOR EFFECTIVE AUDITORY EVOKED RESPONSE

BACKGROUND OF THE INVENTION

The invention relates to the field of auditory evoked response (AER) systems and, more particularly, to AER systems utilizing a wireless EEG system.

The opportunity for successful intervention in language and cognitive disorders would increase if such disorders could be detected early in a child's life. Early detection would allow resources to be focused on remediation when the chances for success are the greatest; in the first months or years of life. Effectively improving children's cognitive capabilities will lead to greater scholastic success which should lead to increased skill sets, greater self esteem and, in turn, reduced poverty. Currently, intervention does not occur until the child has a demonstrated record of failure, typically at age 8-10.

AER is the most accurate technique for early detection of such disorders. When utilized shortly after birth it can predict the language and cognitive skills that the infant will have three years later. AER data taken at birth accounts for 78% of the total variance in predicting McCarthy scores at age three. Accordingly, a simple, easy to use, low cost system to detect language and cognitive skill disabilities at birth is required.

AER utilizes the basic EEG technology and devices to monitor and record a subject's, frequently an infant's or older child's, response to certain auditory stimuli over a prescribed period of time. One disadvantage of this technology is that traditional EEG systems have electrodes with wire leads connected to the monitoring and recording equipment. When performing AER testing of infants, the infants tend to focus on and pull these wire leads creating artifacts making the data inaccurate, increasing the cost of the testing, or, possibly invalidating the test altogether. To make the system convenient to use so that it may be applied in typical hospital and preschool settings, wires to equipment need to be eliminated. A wireless system will eliminate these artifacts, ease donning and doffing, allow the infant or child to be moved to several settings during the testing without attaching and reattaching the system, and allow the testing to be performed over a period of time to allow the mother and child to feed and attend to other bodily functions without having to "stay wired".

Systems have been developed involving wireless EEG transmission. U.S. Pat. No. 5,279,305 teaches such a system. While this patent discloses a device to transmit and receive EEG data by radio frequency telemetry, it requires Manchester encoding which is a system for combining data with its associated clock in a single transmitted data stream. The Manchester encoding is essential to obviate inherent frequency instability of the transmitter taught in the '305 patent, which instability may result in impairment of overall system performance and contravention of FCC regulations. Manchester encoding, though, is limited in that it does not provide for error correction of transmitted signals and cuts the effective data transmission rate in half, thereby reducing data transmission efficiency and capability and transmitted data integrity.

Essential to an AER system is the ability to produce and compare the brain response of a subject to certain audible stimuli. This requires extremely accurate timing of the brain wave response to the stimuli and, therefore, a high degree of transmitted data integrity. The '305 patent, although teaching an effective EEG system, does not teach the accurate timing and transmitted data integrity essential for an effective AER system.

Accordingly, a need exists for an effective AER system which overcomes these disadvantages.

SUMMARY OF THE INVENTION

The present invention provides a system to satisfy the aforementioned need.

Accordingly, an object of the present invention is to provide a wireless EEG system in which voltages produced by the brain electrical activity of a person are sensed by an electrode array attached to a person and a radio frequency signal corresponding to the voltages sensed is produced and transmitted by transmitting means to receiving means. The transmitting means encodes the radio frequency signal with error detecting and correcting encoding and utilizes carrier frequency shift keyed circuitry to modulate a phase locked loop synthesized carrier frequency and reference frequency shift keyed circuitry to modulate a reference frequency to allow for non-return to zero format of the radio frequency signal obviating the need for Manchester encoding. The receiving means receives the radio frequency signal, decodes it and produces a data output corresponding thereto. It outputs the data output to an operator interface which displays the data output graphically.

It is another object of the present invention to provide a wireless EEG system for an effective auditory evoked response in which voltages produced by the brain electrical activity of a person are sensed by an electrode array attached to a person and a radio frequency signal corresponding to the voltages sensed is produced and transmitted by transmitting means to receiving means. The transmitting means encodes the radio frequency signal with error detecting and correcting encoding and utilizes carrier frequency shift keyed circuitry to modulate a phase locked loop synthesized carrier frequency and reference frequency shift keyed circuitry to modulate a reference frequency to allow for non-return to zero format of the radio frequency signal obviating the need for Manchester encoding. The receiving means receives the radio frequency signal, decodes it and produces a data output corresponding thereto. It outputs the data output to an operator interface. The operator interface records a verbal sound given by an individual and provides an auditory stimulus. The operator interface displays the data output and this display provides a comparison of the brain electrical activity in response to the stimulus provided.

BRIEF DESCRIPTION OF THE DRAWINGS

Further features of the present invention will become apparent to those skilled in the art to which the present invention relates from reading the following specification with reference to the accompanying drawings in which.

DETAILED DESCRIPTION OF THE PREFERRED EMBODIMENT

Figure 1:
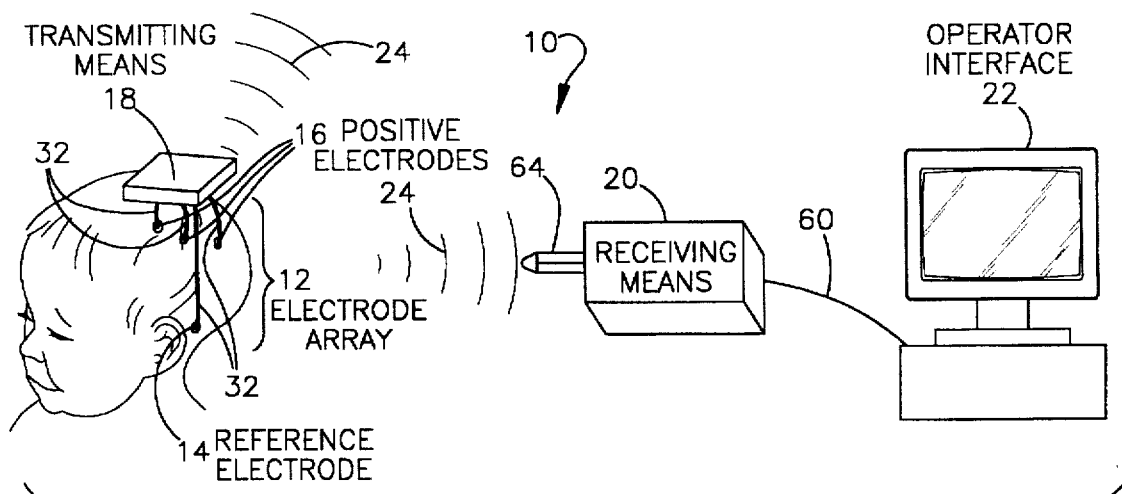
FIG. 1 is a view showing the present invention with the electrode array and the transmitting means attached to an infant's head, the receiving means and the operator interface.

Referring now to the drawings and, more particularly, FIG. 1, there is shown a view of the present invention 10.

The electrode array 12 comprises at least two electrodes; with at least one being a reference electrode 14 and at least one being a positive electrode 16. In the preferred embodiment, the electrode array 12 is shown as three positive electrodes 16 with a reference electrode 14. The electrode array 12 and transmitting means 18 are shown attached to a person's head. In this view an infant is shown but it is understood that the present invention 10 is not limited to an infant. In the preferred embodiment of the present invention, the positive electrodes 16 and reference electrode 14 are gold, but it is not necessary that they be made of that substance. The electrode array 12 is electrically connected by wire leads 32 to the transmitting means 18. The receiving means 20 and operator interface 22 are shown located apart from the person. The receiving means 20 and operator interface 22 are connected by the interface cable 60. The operator interface 22 is, preferably, a personal computer. The electrode array 12 senses voltages produced by the brain electrical activity of the person. The transmitting means 18 produces a radio frequency signal 24 corresponding to the voltages sensed by the electrode array 12 and transmits the radio frequency signal 24 by radio frequency telemetry through a transmitting antenna 26 (not shown on FIG. 1). The receiving means 20, through a receiving antenna 64, receives the radio frequency signal 24 produced and transmitted by transmitting means 18. The receiving means 20 produces a data output 58 (not shown in FIG. 1) corresponding to the radio frequency signal 24 it received. The operator interface 22, by way of the interface cable 60, receives as input the data output 58 produced by the receiving means 20 and displays it graphically.

Figure 2:
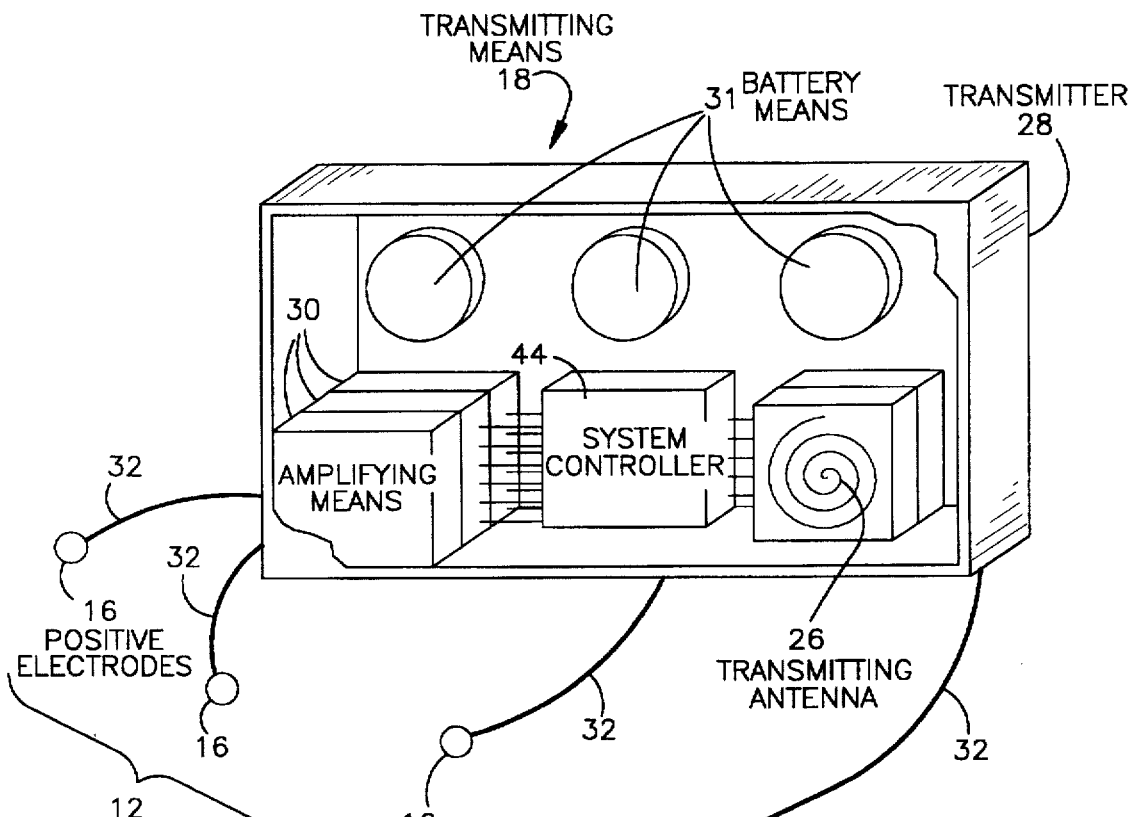
FIG. 2 is a detail view of the electrode array and transmitting means.

Referring now to FIG. 2 there is shown a detail view of the electrode array 12 and transmitting means 18 with the transmitting means 18 cut away to show its internal components. The transmitting means 18 has a transmitting antenna 26, transmitter 28, amplifying means 30, system controller 44 and a battery means 31. In the preferred embodiment, the transmitting antenna 26 is a spiral antenna screen printed on a circuit board. Also, in the preferred embodiment the transmitting means 18 is electrically powered by the battery means 31. While in the preferred embodiment, the battery means 31 comprises three 1.2 volt nickel metal hydride batteries wired in series to provide 3.6 volts with a capacity of 65 mAhr, it is understood that any battery which provides sufficient voltage and capacity can be used. The electrode array 12 is electrically connected to the amplifying means 30 within the transmitting means 18 using wire leads 32. Advantageously, the wire leads 32 will be about one to six inches long; small enough to fit securely under a bandage or cap. The positive electrodes 16 and reference electrode 14 will be located at different areas of the head as the researcher and/or clinician deem appropriate. Typically the reference electrode 14 is placed just behind the ear, while the positive electrodes 16 are located at positions $C_z$, $C_3$ and/or $C_4$ of the person's head. The transmitting means 18 can be adhered directly to the person's head using tape or suction, while an electrode gel or paste is used to hold the electrode array 12 in place and to provide electrical contact with the skin. A bandage, or cap, (not shown in FIG. 2) may be used to cover the entire area to prevent the person from disturbing the electrode array 12 and the transmitting means 18.

Figure 3:
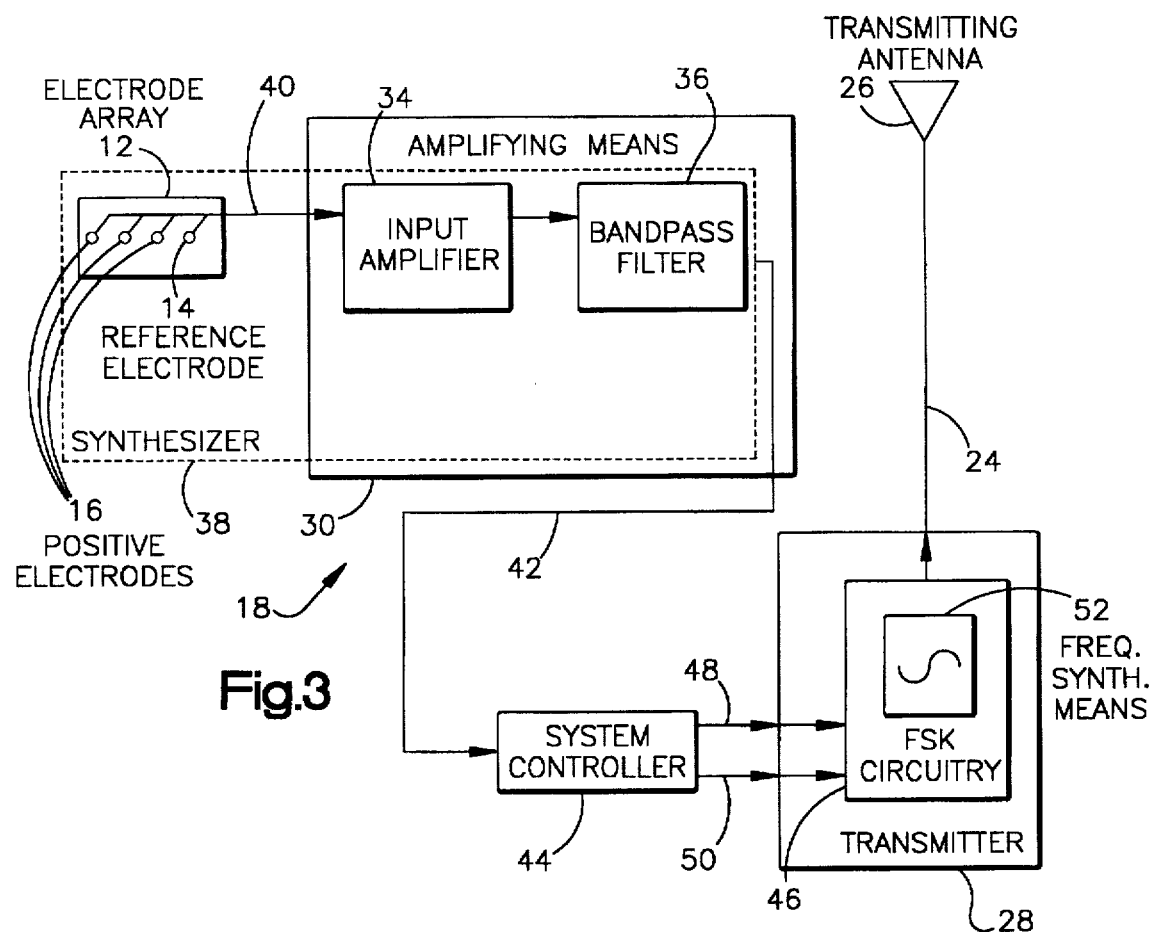
FIG. 3 is a block diagram of the electrode array and the transmitting means.

Referring now to FIG. 3, there is shown a block diagram of the electrode array 12 and the transmitting means 18. In the preferred embodiment, the electrode array 12 can provide to the amplifying means 30 either a differential input, the difference between the status of two positive electrodes 16 in relation to a reference electrode 14, or a single-ended input, the status of one positive electrode 16 in relation to a reference electrode 14. The amplifying means 30 is comprised of at least one input amplifier 34 and at least one bandpass filter 36. The amplifying means 30 receives an electrode signal 40 from the electrode array 12. The electrode signal 40 is a response to changes in the brain electrical activity of the person. In the preferred embodiment, the input amplifier 34 provides an initial gain of 100 to the electrode signal 40, while the bandpass filter 36 has a bandpass of about 0.1 to 36 Hz. and provides an additional gain of about 50 to the electrode signal 40 resulting in an output signal 42 with an overall gain of about 5,000 from the electrode signal 40. A system controller 44 is electrically connected to each of the bandpass filters 36. The output signal 42 from each bandpass filter 36 is inputted to the system controller 44. The system controller 44 provides signal conditioning to the output signal 42 to allow it to be telemetry transmitted. Such signal conditioning includes analog to digital conversion and data encoding thereon. In the preferred embodiment, the system controller 44 employs Hamming encoding, though it is understood that other error correcting code types may be used.

Figure 4:
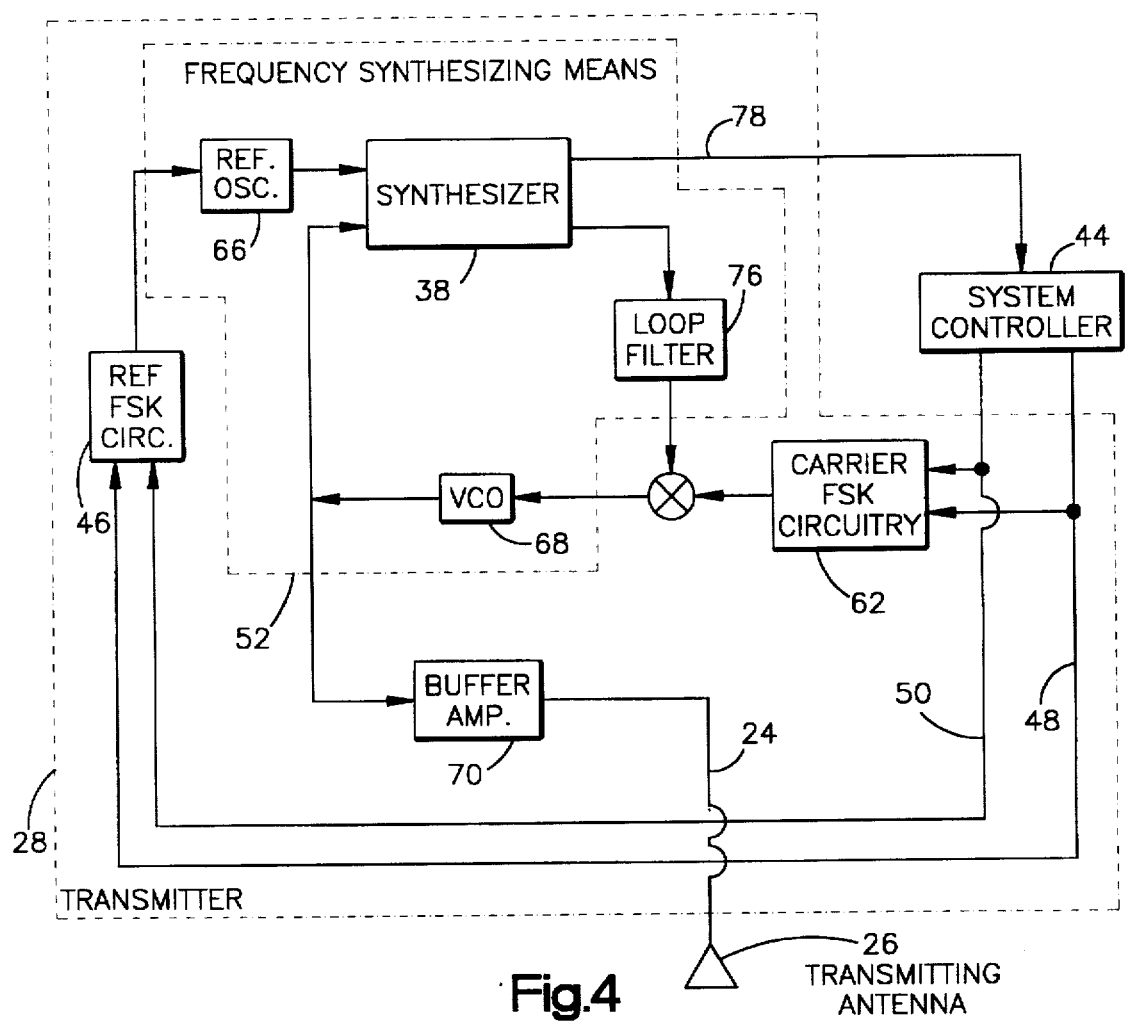
FIG. 4 is a block diagram of the transmitter and system controller.

Referring now to FIG. 4, a block diagram of the transmitter 28 and system controller 44 is shown. In addition to providing signal conditioning, the system controller 44 also controls the transmitter 28 channel frequency thereby controlling the frequency of the radio frequency signal 24 to be transmitted. The system controller 44 outputs a control signal 48, called NowMod*, and a data signal 50 to the transmitter 28. In the preferred embodiment, the transmitter 28 has a buffer amplifier 70 and frequency synthesizing means 52 with a voltage controlled oscillator 68 (VCO) employing phase locked loop (PLL) circuitry with a synthesizer 38 to perform carrier frequency generation. Carrier frequency shift keying circuitry 62 modulates the PLL synthesized carrier frequency of the radio frequency signal 24 in accordance with the data signal 50 and control signal NowMod* 48 outputted from the system controller 44. The control signal 48 starts high and goes low at the instant modulation commences. This results in a positive to zero shift at the moment modulation begins to move the carrier below nominal, so that the data can shift it from that point to a frequency equally spaced on the other side of nominal. The resultant total frequency shift emulates that obtained by using a data signal that goes from negative to positive. Therefore, only zero and positive logic levels are needed to modulate the carrier frequency both above and below the nominal nonmodulated carrier frequency but without the use of a negative supply.

In the preferred embodiment, the reference oscillator 66 is a voltage controlled crystal oscillator (VCXO). Data signal 50 and control signal 48 modulate the reference oscillator 66 utilizing reference frequency shift keying circuitry 46 in the same manner, and by the same percentage, as the carrier frequency shift keying circuitry 62 modulates the carrier frequency of the radio frequency signal 24. Modulation of the reference oscillator 66 is done so the data need not be 50% duty cycle allowing standard non-return to zero (NRZ) format data of any duty cycle to be correctly transmitted. By modulating the reference frequency, the data ideally does not upset the control system action of the PLL, so that the PLL does not detect the modulation as frequency error to be corrected. For this approach to be effective, the modulation bandwidth of the reference oscillator 66 must exceed the loop bandwidth of the PLL synthesizer as established by the loop filter 76. Without the modulation of the reference frequency, the PLL would respond and distort the desired modulation, thus reducing or even destroying the effectiveness of the transmitter 28.

The commonly known method of preventing such distortion without modulating the reference frequency is Manchester encoding of the data. Manchester encoding gives a zero average frequency shift and thus prevents the PLL from responding inappropriately to the data, but at the expense of reducing the data rate by fifty percent. Therefore, one objective of the invention is to maintain the highest data rate possible within a given channel bandwidth by eliminating the requirement of Manchester encoding.

The transmitter 28 is under software control and, in the preferred embodiment, is frequency agile over the 902 to 928 MHz band, although it is understood that other frequency bands may be used. It is the transmitter 28 portion of the transmitting means 18 that transmits the radio frequency signal 24 by way of the transmitting antenna 26.

Figure 5:
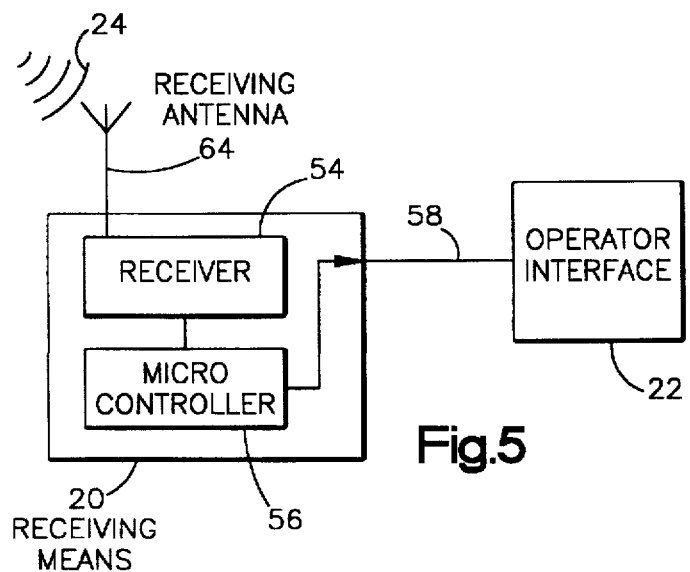
FIG. 5 is a block diagram of the receiving means.

Referring now to FIG. 5 there is shown a block diagram of the receiving means 20 and the operator interface 22. Although any suitable radio frequency receiving means can be used, in the preferred embodiment the receiving means 20 has a receiver 54 which is a superheterodyne type with a plurality of channels. The desired channel is selected via processor control of the frequency of a PLL synthesizer that serves as the first local oscillator. In the preferred embodiment, the receiver 54 employs a frequency shift keyed demodulation format. The receiving means 20 receives the radio frequency signal 24 through receiving antenna 64. The receiving means 20 also has a microcontroller 56 incorporated therein which programs the PLL synthesizer. The receiver 54 outputs data and error correction bits to the microcontroller 56 which removes error correction bits and outputs corrected data as a data output 58 to the operator interface 22. The data output 58 corresponds to the radio frequency signal 24 received by said receiver 54. The receiving means 20 outputs the data output 58 to the operator interface 22. In the preferred embodiment, the operator interface 22 has software programmed in it to record a verbal sound, advantageously in the form of a phoneme, given by an individual and to provide an auditory stimulus. It captures the data output 58 and records and displays it graphically as wave forms of the person as he or she responds to the stimulus comparing the timing of the wave forms with the onset of the stimulus. The operator interface 22 has software which allows complete control over the generation of stimulus phonemes during data collection, allowing for automatic synchronization of the stimulus with the data output 58. Advantageously, the software will generate a preprogrammed sequence of phonemes at appropriate intervals for AER testing.

Now that the invention has been described, variations and modifications will become apparent to those skilled in the art. It is intended that such variations and modifications be encompassed within the scope of the appended claims.

What is claimed is:

1. A wireless EEG system, comprising:
    a) an electrode array having at least two electrodes such that at least one of said electrodes is a reference electrode and at least one of said electrodes is a positive electrode and such that said electrode array is adapted to be attached to a person and senses voltages produced by the brain electrical activity of the person;
    b) transmitting means electrically connected to said electrode array such that said transmitting means produces a radio frequency signal corresponding to the voltages sensed by said electrode array, encodes said radio frequency signal with error detecting and correcting encoding and transmits said radio frequency signal by radio frequency telemetry through a transmitting antenna, said transmitting means utilizing carrier frequency shift keyed circuitry to modulate a phase locked loop synthesized carrier frequency and reference frequency shift keyed circuitry to modulate a reference frequency to allow for non-return to zero format of said radio frequency signal;
    c) receiving means that receives through a receiving antenna said radio frequency signal produced and transmitted by said transmitting means and wherein said receiving means decodes said radio frequency signal and produces a data output corresponding to said radio frequency signal received by said receiving means; and
    d) an operator interface connected to said receiving means such that said operator interface receives as input the data output produced by said receiving means wherein said operator interface displays said data output.

2. The wireless EEG system of claim 1, further comprising, a system controller within said transmitting means such that said system controller conditions said radio frequency signal prior to said transmitting means transmitting said radio frequency signal.

3. The wireless EEG system of claim 2 wherein said system controller outputs a control signal such that said control signal shifts said carrier frequency and said reference frequency by one-half the amount of said frequency shift keyed modulation such that only zero and positive logic levels are needed to modulate said carrier frequency both above and below the nominal nonmodulated carrier frequency.

4. The wireless EEG system of claim 1, further comprising, a microcontroller within said receiving means such that said receiving means is controlled thereby.

5. The wireless EEG system of claim 1 wherein said error correcting encoding is Hamming encoding.

6. The wireless EEG system of claim 1 wherein said electrode array provides a differential input to said transmitting means.

7. The wireless EEG system of claim 1 wherein said electrode array provides a single ended input to said transmitting means.

8. A wireless EEG system for effective auditory evoked response, comprising:
    a) an electrode array having at least two electrodes such that at least one of said electrodes is a reference electrode and at least one of said electrodes is a positive electrode and such that said electrode array is adapted to be attached to a person and senses voltages produced by the brain electrical activity of the person;
    b) transmitting means electrically connected to said electrode array such that said transmitting means produces a radio frequency signal corresponding to the voltages sensed by said electrode array, encodes said radio frequency signal with error detecting and correcting encoding and transmits said radio frequency signal by radio frequency telemetry through a transmitting antenna, said transmitting means utilizing carrier frequency shift keyed circuitry to modulate a phase locked loop synthesized carrier frequency and reference frequency shift keyed circuitry to modulate a reference frequency to allow for non-return to zero format of said radio frequency signal;
    c) receiving means that receives through a receiving antenna said radio frequency signal produced and transmitted by said transmitting means and wherein said receiving means decodes said radio frequency signal and produces a data output corresponding to said radio frequency signal received by said receiving means; and d) an operator interface connected to said receiving means such that said operator interface receives as input the data output produced by said receiving means and such that said operator interface provides an auditory stimulus wherein said operator interface displays said data output with said display providing a comparison of said brain electrical activity in response to said stimulus and such that said operator interface is programmable.

9. The wireless EEG system for effective auditory evoked response of claim 8, further comprising, a system controller within said transmitting means such that said system controller conditions said radio frequency signal prior to said transmitting means transmitting said radio frequency signal and wherein said system controller outputs a control signal such that said control signal shifts said carrier frequency and said reference frequency by one-half the amount of said frequency shift keyed modulation such that only zero and positive logic levels are needed to modulate said carrier frequency both above and below the nominal nonmodulated carrier frequency.

10. The wireless EEG system for effective auditory evoked response of claim 8, further comprising, a microcontroller within said receiving means such that said receiving means is controlled thereby.

11. The wireless EEG system for effective auditory evoked response of claim 8 wherein said error correcting encoding is Hamming encoding.

12. The wireless EEG system for effective auditory evoked response of claim 8 wherein said electrode array provides a differential input to said transmitting means.

13. The wireless EEG system for effective auditory evoked response of claim 8 wherein said electrode array provides a single ended input to said transmitting means.

14. A wireless EEG system for effective auditory evoked response, comprising:

a) an electrode array having at least two electrodes such that at least one of said electrodes is a reference electrode and at least one of said electrodes is a positive electrode and wherein said electrode array is adapted to be attached to a person and senses voltages produced by the brain electrical activity of the person such that an electrode signal is produced in response thereto;

b) transmitting means electrically connected by wire leads to said electrode array, said transmitting means being electrically powered by battery means therein and having a transmitting antenna, transmitter, system controller and amplifying means also located therein wherein said amplifying means increases the gain of said electrode signal, said transmitter produces a radio frequency signal corresponding to said voltages sensed by said electrode array and said system controller conditions said radio frequency signal and encodes an error detection and correcting encoding thereon, said transmitting means utilizing carrier frequency shift keyed circuitry to modulate a phase locked loop synthesized carrier frequency and reference frequency shift keyed circuitry to modulate a reference frequency to allow for non-return to zero format of said radio frequency signal;

c) receiving means having a receiving antenna that receives said radio frequency signal produced and transmitted by said transmitting means and said receiving means being a superheterodyne type having a microcontroller and wherein said receiving means produces a data output corresponding to the radio frequency signal received by said receiving means; and d) an operator interface connected to said receiving means such that said operator interface receives as input the data output produced by said receiving means and such that said operator interface records a verbal sound given by an individual and provides an auditory stimulus and wherein said operator interface displays said data output, said display providing a comparison of said brain electrical activity in response to said stimulus and such that said operator interface is programmable.

15. The wireless EEG system for effective auditory evoked response of claim 14 wherein said system controller outputs a control signal such that said control signal shifts said carrier frequency and said reference frequency by one-half the amount of said frequency shift keyed modulation such that only zero and positive logic levels are needed to modulate said carrier frequency both above and below the nominal nonmodulated carrier frequency.

16. The wireless EEG system for effective auditory evoked response of claim 14, further comprising, a circuit board in said transmitting means whereon said transmitting antenna is screen printed.

17. The wireless EEG system for effective auditory evoked response of claim 14, wherein said amplifying means comprises at least one input amplifier.

18. The wireless EEG system for effective auditory evoked response of claim 14 wherein said amplifying means comprises at least one bandpass filter.

19. The wireless EEG system for effective auditory evoked response of claim 14, further comprising a interface cable which connects the receiving means to the operator interface.

20. The wireless EEG system for effective auditory evoked response of claim 14 wherein said operator interface is a personal computer.

21. The wireless EEG system for effective auditory evoked response of claim 14 wherein said transmitter is software controllable and frequency agile over various allowable radio frequency bands.

22. The wireless EEG system of claim 14 wherein said error correcting encoding is Hamming encoding.

* * * * *